United States Patent
Neumann et al.

(10) Patent No.: US 9,827,198 B2
(45) Date of Patent: Nov. 28, 2017

(54) PHARMACEUTICAL DOSAGE FORMS COMPRISING SODIUM-1-[6-(MORPHOLIN-4-YL)PYRIMIDIN-4-YL]-4-(1H-1,2,3-TRIAZOL-1-YL)-1H-PYRAZOL-5-OLATE

(71) Applicant: Bayer Pharma Aktiengesellschaft, Berlin (DE)

(72) Inventors: Heike Neumann, Wuppertal (DE); Klaus Benke, Bergisch Gladbach (DE); Michael Formell, Glienicke (DE); Gabriele Winter, Glienicke (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 15/029,215

(22) PCT Filed: Oct. 13, 2014

(86) PCT No.: PCT/EP2014/071855
§ 371 (c)(1),
(2) Date: Apr. 13, 2016

(87) PCT Pub. No.: WO2015/055564
PCT Pub. Date: Apr. 23, 2015

(65) Prior Publication Data
US 2016/0256394 A1    Sep. 8, 2016

(30) Foreign Application Priority Data
Oct. 17, 2013    (EP) .................................... 13189145

(51) Int. Cl.
*A61K 9/20* (2006.01)
*A61K 9/28* (2006.01)
*A61K 31/5377* (2006.01)

(52) U.S. Cl.
CPC ............. *A61K 9/2018* (2013.01); *A61K 9/20* (2013.01); *A61K 9/2013* (2013.01); *A61K 9/2054* (2013.01); *A61K 9/2095* (2013.01); *A61K 9/28* (2013.01); *A61K 31/5377* (2013.01)

(58) Field of Classification Search
None
See application file for complete search history.

(56) References Cited

U.S. PATENT DOCUMENTS

2010/0098756 A1* 4/2010 Matsuoka ............ A61K 9/0056
424/465
2012/0129857 A1* 5/2012 Militzer ............... C07D 403/14
514/236.2

FOREIGN PATENT DOCUMENTS

EA    2008/067871 A1    6/2008
WO    2012065967 A1    5/2012

OTHER PUBLICATIONS

"Bekanntmachung zum Europäischen Arzneibuch", Europäisches Arzneibuch, 6. Ausgabe, Grundwerk 2008, 2008, 19 pages.
Bauer, et al., "Lehrbuch der Pharmazeutischen Technologie", Wissenschaftliche Verlagsgesellschaft mbH, Stuttgart, 1999, pp. 305-131.
Ritschel, et al., "Die Tablette: Handbuch der Entwicklung, Herstellung und Qualitatssicherung", Editio Cantor Verlag Aulendorf 2002, pp. 268-314.
European Patent Office, Written Opinion for International Patent No. PCT/EP2014/071855, Apr. 23, 2015, 5 pages.
European Patent Office, International Search Report (with English translation) for International Patent No. PCT/EP2014/071855, Dec. 16, 2014, 5 pages.

* cited by examiner

*Primary Examiner* — Robert A Wax
*Assistant Examiner* — Quanglong Truong
(74) *Attorney, Agent, or Firm* — Nixon & Vanderhye P.C.

(57) ABSTRACT

The present invention relates to solid pharmaceutical dosage forms for oral administration comprising sodium 1-[6-(morpholin-4-yl)pyrimidin-4-yl]-4-(1H-1,2,3-triazol-1-yl)-1H-pyrazol-5-olate (active ingredient (I)), characterized in that the active ingredient (I) is released, and also methods for the preparation thereof, use thereof as medicaments, and also use thereof for prophylaxis, secondary prophylaxis or treatment of disorders, particularly cardiovascular disorders, heart failure, anemia, chronic renal disorders and renal insufficiency.

12 Claims, No Drawings

PHARMACEUTICAL DOSAGE FORMS COMPRISING SODIUM-1-[6-(MORPHOLIN-4-YL)PYRIMIDIN-4-YL]-4-(1H-1,2,3-TRIAZOL-1-YL)-1H-PYRAZOL-5-OLATE

CROSS-REFERENCE TO RELATED APPLICATIONS

This application is a U.S. national phase application of International Patent Application No. PCT/EP2014/071855, filed Oct. 13, 2014 and titled PHARMACEUTICAL DOSAGE FORMS CONTAINING SODIUM-1-[6-(MORPHOLIN-4-YL)PYRIMIDIN-4-YL]-4-(1H-1,2,3-TRIAZOL-1-YL)-1H-PYRAZOL-5-OLATE, which claims priority to European Patent Application No. 13189145.9, filed Oct. 17, 2013 and titled PHARMACEUTICAL DOSAGE FORMS CONTAINING SODIUM-1-[6-(MORPHOLIN-4-YL)PYRIMIDIN-4-YL]-4-(1H-1,2,3-TRIAZOL-1-YL)-1H-PYRAZOL-5-OLATE, the contents of both of which are incorporated herein by reference in their entirety.

The present invention relates to solid pharmaceutical dosage forms for oral administration comprising sodium 1-[6-(morpholin-4-yl)pyrimidin-4-yl]-4-(1H-1,2,3-triazol-1-yl)-1H-pyrazol-5-olate (active ingredient (I)), characterized in that the active ingredient (I) is released, and also methods for the preparation thereof, use thereof as medicaments, and also use thereof for prophylaxis, secondary prophylaxis or treatment of disorders, particularly cardiovascular disorders, heart failure, anaemia, chronic renal disorders and renal insufficiency.

The compound of the formula (II), 1-[6-(morpholin-4-yl)pyrimidin-4-yl]-4-(1H-1,2,3-triazol-1-yl)-1H-pyrazol-5-ol (enol form; formula (IIa)) or 2-[6-(morpholin-4-yl)pyrimidin-4-yl]-4-(1H-1,2,3-triazol-1-yl)-1,2-dihydro-3H-pyrazol-3-one (keto form; formula (IIb)), is known from WO 2008/067871.

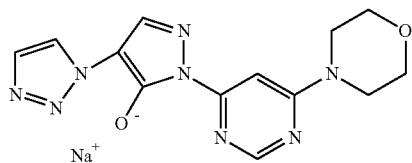

Active ingredient (I)

is the sodium salt of the compound of the formula (II) and shows significantly higher stability with respect to uptake or release of water under varying conditions of atmospheric humidity. Sodium 1-[6-(morpholin-4-yl)pyrimidin-4-yl]-4-(1H-1,2,3-triazol-1-yl)-1H-pyrazol-5-olate (active ingredient (I)) is known from WO 2012/065967. When the active ingredient (I) is discussed below, this therefore means the crystal modification I of sodium 1-[6-(morpholin-4-yl)pyrimidin-4-yl]-4-(1H-1,2,3-triazol-1-yl)-1H-pyrazol-5-olate (I).

To develop a solid pharmaceutical dosage form for oral administration, sodium 1-[6-(morpholin-4-yl)pyrimidin-4-yl]-4-(1H-1,2,3-triazol-1-yl)-1H-pyrazol-5-olate (active ingredient (I)), which does not have this hygroscopicity, is therefore used.

In cases of diseases which require treatment over a lengthy period, or for the long-term prophylaxis of diseases, it is desirable to keep the frequency of intake of medicaments as low as possible and the tablet size as small as possible. This is not only more convenient for the patient, it also increases the reliability of treatment by reducing the disadvantages of irregular intake (improvement in compliance). In order to increase compliance, particularly in older patients, the tablets should be as small as possible, i.e. have a high concentration of active ingredient, particularly with regard to the higher dosage strengths.

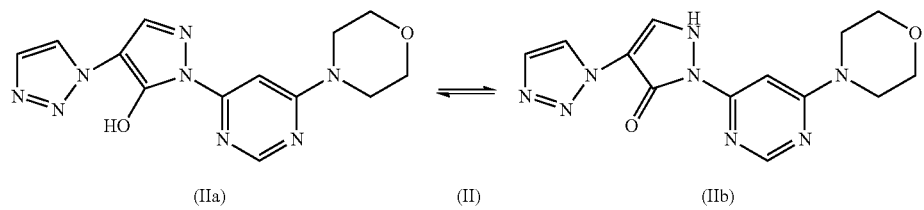 [SMILES: Oc1c(-n2ccnn2)cnn1-c1cc(N2CCOCC2)ncn1 ; O=c1c(-n2ccnn2)c[nH]n1-c1cc(N2CCOCC2)ncn1 ; "(II)"]

(IIa)     (II)     (IIb)

The compound of the formula (II) acts as an inhibitor of HIF prolyl-4-hydroxylases and, owing to this specific mechanism of action, causes, after parenteral or oral administration, the in vivo induction of HIF target genes such as erythropoietin, and the biological processes triggered thereby, such as erythropoiesis.

The active ingredient (I), sodium 1-[6-(morpholin-4-yl)pyrimidin-4-yl]-4-(1H-1,2,3-triazol-1-yl)-1H-pyrazol-5-olate, During the course of development it was found that the increase in the active ingredient concentration of the active ingredient (I) in tablets worsened the release rate of the active ingredient (I) from the tablets, although the tablets were prepared by standard methods known to those skilled in the art.

The aim of the development was, therefore, to identify solid pharmaceutical dosage forms for oral administration comprising sodium 1-[6-(morpholin-4-yl)pyrimidin-4-yl]-4-(1H-1,2,3-triazol-1-yl)-1H-pyrazol-5-olate (active ingredient (I)) at high active ingredient concentration, in order to obtain the smallest possible e.g. tablets also at high active ingredient concentrations.

Surprisingly, the auxiliaries of the pharmaceutical dosage forms have a considerable influence on the release directly after the preparation of the tablets, despite the good water solubility of active ingredient (I). Salt exchanges of the active ingredient (I) into poorly soluble salt forms using customary standard formulations in the solid state had the consequence that the release results declined directly after the preparation of the tablets and after stress testing of the tablets.

Surprisingly, the use of lactose as auxiliary, in tablet cores for example, is not suitable.

Furthermore, the active ingredient (I) at high active ingredient concentrations shows a physical incompatibility with polyethylene glycol used in the film coating.

By means of the present invention, the provision of a stable pharmaceutical dosage form is possible which on the one hand comprises sufficient amount of the active ingredient (I) for its pharmaceutical effect and on the other hand releases the active ingredient (I) rapidly.

During the formulation development, the physicochemical characteristics in combination with the particular biological properties of the active ingredient (I) have been taken into consideration. The salt exchange of the active ingredient (I) [=sodium salt] into poorly soluble salts, for example, is included under physicochemical characteristics.

It has been found that active ingredient (I) tends to form poorly soluble salts in the presence of divalent and trivalent cations whose solubility is only $\frac{1}{100}$ or $\frac{1}{10\,000}$ of the solubility of the sodium salt.

Solubility of various active ingredient salts of the compound of the formula (II):

| Salt | Solubility in water at 25° C. [mg/100 mL] |
|---|---|
| Sodium salt (active ingredient (I)) | 2625 |
| Magnesium salt | 4 |
| Iron(II) salt | 0.2 |
| Calcium salt | 27 |
| Iron(III) salt | 19 |
| Aluminium salt | 6 |

This has the consequence that salt exchange of the active ingredient (I) in the solid state significantly worsens the release results of the active ingredient (I) after storage of e.g. tablets. This worsening is particularly apparent at high active ingredient concentrations.

The salt exchange of the active ingredient (I) in the development of solid pharmaceutical dosage forms for oral administration comprising the active ingredient (I) must be prevented.

In the context of the present invention, the concentration of the active ingredient (I) is determined by means of the active ingredient (I) (sodium salt).

A tablet dose of 100 mg, i.e. 100 mg of the compound of the formula (II), corresponds to 107 mg of the active ingredient (I) (sodium salt).

In the context of the present invention, a high active ingredient concentration means a concentration of active ingredient (I) ≥10% based on the total mass of the formulation.

The present invention provides solid pharmaceutical dosage forms for oral administration comprising sodium 1-[6-(morpholin-4-yl)pyrimidin-4-yl]-4-(1H-1,2,3-triazol-1-yl)-1H-pyrazol-5-olate (active ingredient (I)), characterized in that (a) the concentration of auxiliaries having divalent and/or trivalent cations is ≤0.1% based on the total mass of the formulation, (b) the concentration of lactose is ≤10% based on the total mass of the formulation, (c) the concentration of active ingredient (I) is ≥10% based on the total mass of the formulation, and (d) if the dosage form has a film coating, said film coating does not comprise polyethylene glycol.

In the context of the present invention, auxiliaries are binders, fillers and dry binders, disintegration promoters and lubricants.

An auxiliary having divalent and/or trivalent cations is, for example, magnesium stearate.

In the context of the present invention, at least one filler and at least one lubricant are present in the solid pharmaceutical dosage forms for oral administration as auxiliaries.

The film coating comprises coating and/or film-forming agents and/or colourants/pigments. These constituents of the film coating may optionally contain divalent and/or trivalent cations.

Colourants/pigments having divalent and/or trivalent cations are, for example, titanium dioxide and iron oxide.

In the context of the present invention, the tablets are composed of a tablet core and the tablet core optionally has a film coating. The tablet core comprises the active ingredient (I), at least one filler and at least one lubricant and optionally further auxiliaries. The tablets preferably have a film coating.

The tablets preferably have a film coating which does not comprise polyethylene glycol.

The inventive solid pharmaceutical dosage form for oral administration preferably comprises, for example, granules, hard gelatin capsules filled with granules, sachets or tablets; preference is given to tablets. Particular preference is given to rapid-release tablets of active ingredient (I).

In the context of the present invention, rapid-release tablets are particularly those which have released at least 85% of active ingredient (I) per test specimen into the release medium after 30 minutes, from 6 test specimens, according to the release method of the European Pharmacopoeia using apparatus 2 (paddle). The rotation speed of the stirrer is 50 rpm (revolutions per minute) in the release medium consisting of 900 ml of 0.1N hydrochloric acid. This method is used for rapid-release tablets in which the tablet dose is ≤100 mg (corresponding to 107 mg of the active ingredient (I) (sodium salt)) in order to ensure sink conditions in the release medium. Sink conditions are understood to mean the threefold volume of release medium which would be required to prepare a saturated solution of the amount of active ingredient contained in the tablet.

Particular preference is given to such rapid-release tablets, which have released at least 85% of active ingredient (I) per test specimen into the release medium after 30 minutes, from 6 test specimens, according to the release method of the European Pharmacopoeia using apparatus 2 (paddle), following 1 month open storage at 40° C. and 75% relative humidity.

The present invention provides solid pharmaceutical dosage forms for oral administration comprising sodium 1-[6-(morpholin-4-yl)pyrimidin-4-yl]-4-(1H-1,2,3-triazol-1-yl)-1H-pyrazol-5-olate (active ingredient (I)), characterized in that (a) the concentration of auxiliaries having divalent and/or trivalent cations is ≤0.1% based on the total mass of the formulation,
(b) the concentration of lactose is ≤10% based on the total mass of the formulation,
(c) the concentration of active ingredient (I) is ≥10% based on the total mass of the formulation,
(d) if the dosage form has a film coating, said film coating does not comprise polyethylene glycol, and
(e) the active ingredient (I) is released rapidly.

The present invention provides solid pharmaceutical dosage forms for oral administration comprising sodium 1-[6-(morpholin-4-yl)pyrimidin-4-yl]-4-(1H-1,2,3-triazol-1-yl)-1H-pyrazol-5-olate (active ingredient (I)), characterized in that
(a) the concentration of auxiliaries having divalent and/or trivalent cations is ≤0.1% based on the total mass of the formulation,
(b) the concentration of lactose is ≤10% based on the total mass of the formulation,
(c) the concentration of active ingredient (I) is ≥10% based on the total mass of the formulation,
(d) if the dosage form has a film coating, said film coating does not comprise polyethylene glycol, and
(e) the active ingredient (I) is released rapidly,
wherein at least 85% of active ingredient (I) are released per test specimen into the release medium after 30 minutes, from 6 test specimens relating to the pharmaceutical dosage form, according to the release method of the European Pharmacopoeia using apparatus 2 (paddle).

The active ingredient (I) is present in the crystal modification, in which the active ingredient (I) is obtained in the preparation in the manner described according to WO 2012/065967 under example 1 and is referred to as modification I in the context of the present invention.

The active ingredient (I) is present in the pharmaceutical dosage forms according to the invention in crystalline form. In a particularly preferred embodiment of the present invention, the crystalline active ingredient (I) is used in a micronized form of the crystal modification I. In this case, the active ingredient (I) preferably has a mean particle size $X_{50}$ (50% proportion) less than 10 μm, particularly between 1 and 8 μm, and also an $X_{90}$ value (90% proportion) less than 20 μm.

The active ingredient (I) is present in the pharmaceutical dosage form according to the invention at a concentration of ≥10% based on the total mass of the formulation, preferably in a concentration of 10 to 50% based on the total mass of the formulation, particularly preferably in a concentration of 10 to 40% based on the total mass of the formulation, especially preferably in a concentration of 15 to 30% based on the total mass of the formulation.

Lactose is present in the pharmaceutical dosage form according to the invention at a concentration of ≤10% based on the total mass of the formulation, preferably in a concentration of 0 to 5% based on the total mass of the formulation, particularly preferably no lactose is present.

Auxiliaries having divalent and/or trivalent cations are present in the pharmaceutical dosage form according to the invention at a concentration of ≤0.1% based on the total mass of the formulation, preferably in a concentration of 0 to 0.05% based on the total mass of the formulation, particularly preferably no auxiliaries having divalent and/or trivalent cations are present.

The present invention relates to a method for preparing a solid pharmaceutical dosage form for oral administration comprising sodium 1-[6-(morpholin-4-yl)pyrimidin-4-yl]-4-(1H-1,2,3-triazol-1-yl)-1H-pyrazol-5-olate (active ingredient (I)), a concentration of auxiliaries having divalent and/or trivalent cations ≤0.1% based on the total mass of the formulation, a concentration of lactose ≤10% based on the total mass of the formulation and a concentration of active ingredient (I) ≥10% based on the total mass of the formulation, characterized in that
(a) a granulate comprising the active ingredient (I) is initially prepared
(b) and the granulate, optionally with addition of pharmaceutically acceptable auxiliaries, is then converted into the pharmaceutical dosage form.

The present invention relates to a method for preparing a solid pharmaceutical dosage form for oral administration comprising sodium 1-[6-(morpholin-4-yl)pyrimidin-4-yl]-4-(1H-1,2,3-triazol-1-yl)-1H-pyrazol-5-olate (active ingredient (I)), a concentration of auxiliaries having divalent and/or trivalent cations ≤0.1% based on the total mass of the formulation, a concentration of lactose ≤10% based on the total mass of the formulation and a concentration of active ingredient (I) ≥10% based on the total mass of the formulation, characterized in that
(a) a granulate comprising the active ingredient (I) is initially prepared
(b) and the granulate, optionally with addition of pharmaceutically acceptable auxiliaries, is then converted into the pharmaceutical dosage form,
and wherein at least 85% of active ingredient (I) are released per test specimen into the release medium after 30 minutes, from 6 test specimens relating to the pharmaceutical dosage form, according to the release method of the European Pharmacopoeia using apparatus 2 (paddle).

The granulate may be prepared in method step (a) by wet granulation in a mixer (=mixer granulation) or in a fluidized bed (=fluidized bed granulation) or by dry granulation by means of roller compacting; wet granulation is preferred as fluidized bed granulation.

In the wet granulation process, the active ingredient (I) may either be charged as a solid in the premix (initial charge) or it can be suspended in the granulating fluid or it is incorporated in part in the initial charge and the other part in the granulating fluid. The active ingredient (I) is preferably charged in the premix (initial charge).

The granulating fluid used in accordance with the invention comprises a solvent and a hydrophilic binder. The hydrophilic binder is here dispersed in the granulating fluid or preferably dissolved therein.

Organic solvents, such as ethanol or acetone or water or mixtures thereof, may be used as solvent for the granulating fluid. The solvent used is preferably water.

The hydrophilic binders used are pharmaceutically acceptable hydrophilic additives, preferably those which dissolve in the solvent of the granulating fluid. Preference is given to using hydrophilic polymers here such as hydroxypropylmethylcellulose (HPMC), sodium carboxymethylcellulose, methylcellulose, hydroxypropylcellulose (HPC), low-substituted hydroxypropylcellulose (L-HPC), hydroxypropylcellulose LF, polyvinylpyrrolidone, polyvinyl alcohol, vinylpyrrolidone-vinyl acetate copolymers (for example Kollidon® VA64, BASF), gelatin, guar gum, partially hydrolyzed starch, alginates or xanthan. Preference is given to using hydroxypropylmethylcellulose (HPMC) as hydrophilic binder.

The hydrophilic binder is present in this case at a concentration of 1 to 12% (based on the total mass of the pharmaceutical dosage form), preferably 1 to 6%.

In the premix (initial charge) of the wet granulation, further pharmaceutically acceptable additives are present, such as fillers, dry binders and disintegration promoters (disintegrants).

Fillers and dry binders are, for example, cellulose powder, microcrystalline cellulose, silicified microcrystalline cellulose, mannitol, maltitol, sorbitol and xylitol, preferably microcrystalline cellulose or mannitol or a mixture of microcrystalline cellulose and mannitol.

Disintegration promoters (disintegrants) are, for example, carboxymethylcellulose, croscarmellose (crosslinked carboxymethylcellulose), crospovidone (crosslinked polyvinylpyrrolidone), low-substituted hydroxypropylcellulose (L-HPC), sodium carboxymethyl starch, potato sodium starch glycolate, partially hydrolyzed starch, wheat starch, maize starch, rice starch and potato starch.

The granulate obtained in method step (a) is then converted into the inventive pharmaceutical dosage form in method step (b).

Method step (b) comprises, for example, tabletting, filling into capsules, preferably hard gelatin capsules, or filling as sachets, in each case according to customary methods familiar to those skilled in the art, optionally with addition of further pharmaceutically acceptable additives.

Examples of pharmaceutically acceptable additives are, for example, lubricants, glidants, flow regulators and disintegration promoters (disintegrants).

Lubricants, glidants and flow regulators are, for example, fumaric acid, stearic acid, sodium stearyl fumarate, higher molecular weight fatty alcohols, starches (wheat, rice, maize or potato starch), talc, highly-dispersed (colloidal) silicon dioxide and glyceryl distearate, preferably sodium stearyl fumarate or glyceryl distearate, especially preferably sodium stearyl fumarate.

Disintegration promoters (disintegrants) are, for example, carboxymethylcellulose, croscarmellose (crosslinked carboxymethylcellulose), crospovidone (crosslinked polyvinylpyrrolidone), low-substituted hydroxypropylcellulose (L-HPC), sodium carboxymethyl starch, partially hydrolyzed starch, wheat starch, maize starch, rice starch and potato starch.

The granules or tablets according to the invention are optionally coated in a further step using customary conditions familiar to those skilled in the art. The coating is effected by addition of customary coating and film-forming agents familiar to those skilled in the art, such as hydroxypropylcellulose, hydroxypropylmethylcellulose (for example hydroxypropylmethylcellulose 5 cP or 15 cP), polyvinylpyrrolidone, vinylpyrrolidone-vinyl acetate copolymers (for example Kollidon® VA64, BASF), shellac, glyceryl triacetate, triethyl citrate, talc and/or colourants/pigments such as titanium dioxide, iron oxides, indigotin or suitable colour lacquers.

The wet granulation is described in:
1) W. A. Ritschel, A. Bauer-Brandl, "Die Tablette" (Tablets), Edition Cantor Verlag, 2nd Edition, 2002, pages 268-314.
2) K. H. Bauer, K.-H. Frömming, C. Führer, "Lehrbuch der pharmazeutischen Technologie" (Textbook of pharmaceutical technology), Wissenschaftliche Verlagsgesellschaft mbH Stuttgart, 6th Edition, 1999, pages 305-313.

Active ingredient (I) and auxiliaries may be also mixed and tabletted directly (direct tabletting).

The tabletting is preferably carried out with the granulate initially prepared.

It was further found, surprisingly, in the context of the tablet development, that the effect of light on the active ingredient (I) or the tablet cores produces a brown discolouration. Therefore, a coating of the drug form is advantageous for adequate light protection.

The present invention further provides medicaments comprising a solid pharmaceutical dosage form for oral administration in accordance with the invention comprising the active ingredient (I).

The present invention further relates to the use of solid pharmaceutical dosage forms for oral administration in accordance with the invention comprising the active ingredient (I) and for preparing a medicament for prophylaxis, secondary prophylaxis and/or treatment of disorders, particularly cardiovascular disorders, heart failure, anaemia, chronic renal disorders and renal insufficiency.

The present invention further relates to the use of solid pharmaceutical dosage forms for oral administration in accordance with the invention comprising the active ingredient (I) for prophylaxis, secondary prophylaxis and/or treatment of disorders, particularly cardiovascular disorders, heart failure, anaemia, chronic renal disorders and renal insufficiency.

The present invention further relates to the use of sodium 1-[6-(morpholin-4-yl)pyrimidin-4-yl]-4-(1H-1,2,3-triazol-1-yl)-1H-pyrazol-5-olate (I) for preparing a solid pharmaceutical dosage form for oral administration according to the invention.

The present invention further relates to a method for prophylaxis, secondary prophylaxis and/or treatment of cardiovascular disorders, heart failure, anaemia, chronic renal disorders and renal insufficiency by administration of a solid pharmaceutical dosage form for oral administration in accordance with the invention comprising the active ingredient (I).

Below, the invention is illustrated in detail by preferred working examples; however, the invention is not limited to these examples. Unless indicated otherwise, all amounts given refer to percent by weight.

EXPERIMENTAL PART

1. Release Method

According to the European Pharmacopoeia, 6th Edition, revision 2008, the drug form is tested with apparatus 2 (paddle). The rotation speed of the stirrer is 50 rpm (revolutions per minute) in 900 ml of 0.1N hydrochloric acid. The release criterion is then fulfilled if all 6 test specimens have released at least 85% of active ingredient (I) into the release medium after an investigation period of 30 minutes. This method is used for rapid-release tablets in which the tablet dose is ≤100 mg (corresponding to 107 mg of the active ingredient (I) (sodium salt)) in order to ensure sink conditions in the release medium. Sink conditions are understood to mean the threefold volume of release medium which would be required to prepare a saturated solution of the amount of active ingredient contained in the tablet.

2. Determination of the Fracture Resistance

According to the European Pharmacopoeia, 6th Edition, revision 2008, the force required to fracture tablets under pressure is measured. The measuring instrument consists of two jaws facing each other. One of the jaws moves over the other. The jaw surfaces are flat and larger than the contact zone for the tablet and also are arranged perpendicularly to the direction of motion. The instrument is calibrated with a system having an accuracy of about 1 Newton. The tablet is placed between the jaws, wherein, if appropriate, the shape, the scores and the embossing are taken into account. For each measurement, the tablet is oriented in the same manner relative to the direction of force. The test is carried out on 10 tablets. Tablet fragments must be removed before each test.

3. Fluidized Bed Granulation Preparation Method

Examples 6-1, 6-2, 6-8, 6-9 and 6-10

The binder is dissolved in water and the active ingredient (I) is suspended in this solution. In the course of a fluidized bed granulation, this suspension is sprayed as granulating fluid on the initial charge composed of fillers, optionally lactose and 50% of the disintegration promoter. After drying and sieving (mesh size 0.8 mm) the resulting granules, the other 50% of the disintegration promoter and a lubricant, which is optionally also magnesium stearate, are added and mixed. The ready to press granulate thus obtained is compressed to produce tablets. The tablets are then coated with pigments which are suspended in an aqueous solution composed of coating and film-forming agents and optionally polyethylene glycol.

Example 6-3

The binder is dissolved in water and the active ingredient (I) is suspended in this solution. In the course of a fluidized bed granulation, this suspension is sprayed as granulating fluid on the initial charge composed of fillers, lactose and disintegration promoters. After drying and sieving (mesh size 0.8 mm) the resulting granules, a lubricant is added and mixed. The ready to press granulate thus obtained is compressed to produce tablets.

Examples 6-4 and 6-5

The binder is dissolved in water. In the course of a fluidized bed granulation, this binder solution is sprayed as granulating fluid on the initial charge composed of active ingredient (I) and fillers and optionally lactose. After drying and sieving (mesh size 0.8 mm) the resulting granules, disintegration promoter and magnesium stearate are added and mixed. The ready to press granulate thus obtained is compressed to produce tablets.

Examples 6-6 and 6-7

The binder is dissolved in water and 50% of the active ingredient (I) is suspended in this solution. In the course of a fluidized bed granulation, this suspension is sprayed as granulating fluid on the initial charge composed of 50% of active ingredient (I) and fillers and 50% of the disintegration promoter. After drying and sieving (mesh size 0.8 mm) the resulting granules, the other 50% of the disintegration promoter and magnesium stearate are added and mixed. The ready to press granulate thus obtained is compressed to produce tablets. The tablets are then coated with pigments which are suspended in an aqueous solution composed of coating and film-forming agents and polyethylene glycol.

Examples 6-11, 6-12, 6-15, 6-16, 6-17, 6-18 and 6-19

The binder is dissolved in water. In the course of a fluidized bed granulation, this binder solution is sprayed as granulating fluid on the initial charge composed of active ingredient (I) and fillers, optionally lactose and disintegration promoter. After drying and sieving (mesh size 0.8 mm) the resulting granules, a lubricant is added and mixed. The ready to press granulate thus obtained is compressed to produce tablets. The tablets are then optionally coated with pigments which are suspended in an aqueous solution composed of coating and film-forming agents.

Example 6-21

The binder is dissolved in water. In the course of a fluidized bed granulation, this binder solution is sprayed as granulating fluid on the initial charge composed of active ingredient (I), the fillers and the disintegration promoter. After drying and sieving (mesh size 0.8 mm) the resulting granules, firstly the slipping agent and then the lubricant are added and mixed in a two-stage process. The ready to press granulate thus obtained is compressed to produce tablets. The tablets are then coated with pigments which are suspended in an aqueous solution composed of coating and film-forming agents.

4. Mixer Granulation Preparation Method

Examples 6-13 and 6-14

In a rapid mixer, active ingredient (I), fillers and ca. 40% of the disintegration promoter are mixed (granulate initial charge). A 3% binder solution is prepared and added as granulating fluid to the granulate initial charge. The whole mixture is uniformly mixed with the aid of a rapidly-rotating stirrer. After mixing, the moist granulate is sieved (mesh size 2 mm) and dried. After sieving the dried granulate (mesh size 0.8 mm), the latter is then mixed with ca. 60% of the disintegration promoter and magnesium stearate, which is carried out in two separate mixing steps. The ready to press granulate thus obtained is compressed to produce tablets.

5. Roller Compaction Preparation Method

Example 6-20

Active ingredient (I), filler, disintegration promoter and dry binder are mixed in a free-fall mixer. The powder mixture is sieved (mesh size 1.0 mm) and subsequently mixed again in a free-fall mixer. Sieved highly-dispersed silicon dioxide is added and distributed homogeneously by mixing. Prior to the latter mixing step, magnesium stearate is added. The final mixture thus obtained is dry-granulated by roller compacting and the granulate subsequently compressed to give tablets.

| Abbreviations | |
|---|---|
| Hydroxypropylmethylcellulose 5 cP (HPMC 5 cP) | a 2% aqueous solution of HPMC 5 cP has a viscosity of 5 mPas at 20° C. |
| Hydroxypropylcellulose LF (HPC LF) | a 5% aqueous solution of HPC LF has a viscosity of 75-150 mPas at 20° C. |
| Hydroxypropylmethylcellulose 3 cP (HPMC 3 cP) | a 2% aqueous solution of HPMC 3 cP has a viscosity of 2.4-3.6 mPas at 20° C. |
| RC | Radius of curvature |
| Mn | Mean |
| RH | Relative humidity |
| N | Newton |

6. Compositions of the Dosage Form in Mg/Tablet

|  | 6-1 | 6-2 | 6-3 | 6-4 | 6-5 | 6-6 | 6-7 |
|---|---|---|---|---|---|---|---|
| Active ingredient (I) | 5.35 | 21.4 | 32.1 | 32.1 | 32.1 | 53.5 | 107.0 |
| Binder | | | | | | | |
| Hydroxypropyl methylcellulose 5 cP | 2.25 | 9.0 | 4.5 | 4.5 | 4.5 | 6.3 | 12.6 |
| Hydroxypropyl cellulose LF | — | — | — | — | — | — | — |
| Hydroxypropyl methylcellulose 3 cP | — | — | — | — | — | — | — |
| Fillers and dry binders | | | | | | | |
| Microcrystalline cellulose | 25.5 | 102.0 | 46.8 | 42.3 | 42.0 | — | — |
| Lactose monohydrate | 21.5 | 86.0 | 31.2 | 31.2 | — | — | — |
| Mannitol | — | — | — | — | 31.2 | 128.0 | 256.0 |
| Disintegration promoter | | | | | | | |
| Sodium croscarmellose | 5.0 | 20.0 | 4.5 | 9.0 | 9.0 | 17.5 | 35.0 |
| Lubricant, slipping agent, flow regulator | | | | | | | |
| Magnesium stearate | 0.4 | 1.6 | 0.9 | 0.9 | 1.2 | 4.7 | 9.4 |
| Sodium stearyl fumarate | — | — | — | — | — | — | — |
| Glyceryl distearate | — | — | — | — | — | — | — |
| Highly-dispersed silicon dioxide | — | — | — | — | — | — | — |
| Coating and film-forming agents and colourants/pigments | | | | | | | |
| Hydroxypropyl methylcellulose 5 cP | 0.88 | 3.54 | — | — | — | 2.5 | 5.0 |
| Polyethylene glycol 6000 | 0.18 | 0.71 | — | — | — | — | — |
| Polyethylene glycol 3350 | — | — | — | — | — | 0.5 | 1.0 |
| Red iron oxide | — | — | — | — | — | — | — |
| Yellow iron oxide | 0.10 | 0.42 | — | — | — | 0.3 | 0.6 |
| Talc | 0.18 | 0.71 | — | — | — | 0.5 | 1.0 |
| Titanium dioxide | 0.41 | 1.62 | — | — | — | 1.2 | 2.4 |
| Total | 61.75 | 247.0 | 120.0 | 120.0 | 120.0 | 215.0 | 430.0 |
| Format (mm) | 5WR6 | 9WR15 | | 7WR10 | | 12 × 6 WR5 + 2 | 16 × 7 WR7 + 2 |
| Core fracture resistance (N) [Mn] | 52 | 90 | 69 | 77 | 73 | 95 | 105 |

|  | 6-8 | 6-9 | 6-10 | 6-11 | 6-12 | 6-13 | 6-14 |
|---|---|---|---|---|---|---|---|
| Active ingredient (I) | 53.5 | 53.5 | 53.5 | 26.75 | 80.25 | 53.5 | 53.5 |
| Binder | | | | | | | |
| Hydroxypropyl methylcellulose 5 cP | 6.3 | 6.3 | 6.3 | 3.75 | 11.25 | 5.4 | 7.5 |
| Hydroxypropyl cellulose LF | — | — | — | — | — | — | — |
| Hydroxypropyl methylcellulose 3 cP | — | — | — | — | — | — | — |
| Fillers and dry binders | | | | | | | |
| Microcrystalline cellulose | — | — | — | 50.0 | 150.0 | 115.4 | 160.3 |
| Lactose | — | — | — | — | — | — | — |

-continued

| | | | | | | | |
|---|---|---|---|---|---|---|---|
| monohydrate | | | | | | | |
| Mannitol | 128.0 | 128.0 | 128.0 | 35.75 | 107.25 | — | — |
| *Disintegration promoter* | | | | | | | |
| Sodium croscarmellose | 17.5 | 17.5 | 17.5 | 6.25 | 18.75 | 18.9 | 26.2 |
| *Lubricant, slipping agent, flow regulator* | | | | | | | |
| Magnesium stearate | 4.7 | — | — | — | — | 1.8 | 2.5 |
| Sodium stearyl fumarate | — | 4.7 | — | 2.5 | 7.5 | — | — |
| Glyceryl distearate | — | — | 9.5 | — | — | — | — |
| Highly-dispersed silicon dioxide | — | — | — | — | — | — | — |
| *Coating and film-forming agents and colourants/pigments* | | | | | | | |
| Hydroxypropyl methylcellulose 5 cP | — | — | — | 2.0 | 4.0 | — | — |
| Polyethylene glycol 6000 | — | — | — | — | — | — | — |
| Polyethylene glycol 3350 | — | — | — | — | — | — | — |
| Red iron oxide | — | — | — | 0.2 | 0.4 | — | — |
| Yellow iron oxide | — | — | — | — | — | — | — |
| Talc | — | — | — | 0.4 | 0.8 | — | — |
| Titanium dioxide | — | — | — | 1.4 | 2.8 | — | — |
| Total | 210.0 | 210.0 | 219.5 | 129.0 | 383.0 | 195.0 | 250.0 |
| Format (mm) | 12 × 6WR5 + 2 | | | 7WR10 | 14 × 7 WR6 + 2 | 8WR12 | 9WR15 |
| Core fracture resistance (N) [Mn] | 107 | 106 | 79 | 60 | 129 | 67 | 69 |

| | 6-15 | 6-16 | 6-17 | 6-18 | 6-19 | 6-20 | 6-21 |
|---|---|---|---|---|---|---|---|
| Active ingredient (I) | 53.5 | 53.5 | 53.5 | 53.5 | 53.5 | 53.5 | 80.25 |
| *Binder* | | | | | | | |
| Hydroxypropyl methylcellulose 5 cP | 7.5 | 7.5 | 10.5 | 5.4 | 5.4 | — | — |
| Hydroxypropyl cellulose LF | — | — | — | — | — | 6.25 | — |
| Hydroxypropyl methylcellulose 3 cP | — | — | — | — | — | — | 11.25 |
| *Fillers and dry binders* | | | | | | | |
| Microcrystalline cellulose | 100.0 | 100.0 | 129.0 | 64.0 | 64.0 | 174.0 | 150.0 |
| Lactose monohydrate | — | 69.0 | 129.0 | — | 42.7 | — | — |
| Mannitol | 69.0 | — | — | 42.7 | — | — | 99.0 |
| *Disintegration promoter* | | | | | | | |
| Sodium croscarmellose | 12.5 | 12.5 | 17.5 | 9.0 | 9.0 | 12.5 | 18.75 |
| *Lubricant, slipping agent, flow regulator* | | | | | | | |
| Magnesium stearate | — | — | — | — | — | 2.5 | — |
| Sodium stearyl fumarate | 7.5 | 7.5 | 10.5 | 5.4 | 5.4 | — | 15.0 |
| Glyceryl distearate | — | — | — | — | — | — | — |
| Highly-dispersed silicon dioxide | — | — | — | — | — | 1.25 | 0.75 |

Coating and film-forming agents and colourants/pigments

| | | | | | | | |
|---|---|---|---|---|---|---|---|
| Hydroxypropyl methylcellulose 5 cP | — | — | — | — | — | — | 4.0 |
| Polyethylene glycol 6000 | — | — | — | — | — | — | — |
| Polyethylene glycol 3350 | — | — | — | — | — | — | — |
| Red iron oxide | — | — | — | — | — | — | 0.4 |
| Yellow iron oxide | — | — | — | — | — | — | — |
| Talc | — | — | — | — | — | — | 0.8 |
| Titanium dioxide | — | — | — | — | — | — | 2.8 |
| Total | 250.0 | 250.0 | 350.0 | 180.0 | 180.0 | 250.0 | 383.0 |
| Format (mm) | 9WR15 | 9WR15 | 14 × 7 WR6 + 2 | 8WR12 | 8WR12 | 12 × 6 WR5 + 2 | 14 × 7 WR6 + 2 |
| Core fracture resistance (N) [Mn] | 80 | 79 | 95 | 80 | 82 | 88 | 135 |

7. Release Results after Preparation of the Tablets

| Tablet according to example | Release after 30 min Min/Max/Mean (n = 6) | Release criterion fulfilled |
|---|---|---|
| 6-1 | 100/104/101 | Yes |
| 6-2 | 94/99/98 | Yes |
| 6-3 | 38/69/59 | No |
| 6-4 | 64/74/71 | No |
| 6-5 | 87/91/90 | Yes |
| 6-6 | 91/96/94 | Yes |
| 6-7 | 91/95/94 | Yes |
| 6-8 | 98/100/98 | Yes |
| 6-9 | 99/100/99 | Yes |
| 6-10 | 93/96/95 | Yes |
| 6-11 | 99/101/99 | Yes |
| 6-12 | 88/97/94 | Yes |
| 6-13 | 93/95/94 | Yes |
| 6-14 | 94/97/96 | Yes |
| 6-15 | 94/95/94 | Yes |
| 6-16 | 84/95/91 | No |
| 6-17 | 76/92/87 | No |
| 6-18 | 93/95/95 | Yes |
| 6-19 | 81/92/86 | No |
| 6-20 | 93/97/95 | Yes |
| 6-21 | 85/96/91 | Yes |

8. Release Results after Stress Testing of the Tablet

| Tablet according to example | Release after 30 min Min/Max/Mean (n = 6) | Release criterion fulfilled | Conditions |
|---|---|---|---|
| 6-1 | 98/103/101 | Yes | 1 month 40° C./75% RH, in flask without lid (open storage) |
| 6-6 | 4/20/12 | No | 1 month 40° C./75% RH, in flask without lid (open storage) |
| 6-8 | 80/91/86 | No | 1 month 40° C./75% RH, in flask without lid (open storage) |
| 6-9 | 97/99/99 | Yes | 1 month 40° C./75% RH, in flask without lid (open storage) |
| 6-10 | 91/97/93 | Yes | 1 month 40° C./75% RH, in flask without lid (open storage) |
| 6-11 | 90/97/94 | Yes | 1 month 40° C./75% RH, in flask without lid (open storage) |
| 6-12 | 89/95/93 | Yes | 1 month 40° C./75% RH, in flask without lid (open storage) |

Examples 6-1 and 6-2 are tablets with low concentrations of active ingredient (I) and serve as comparative examples. In these examples, the concentration of active ingredient (I) is below 10% based on the total mass of the formulation. These tablets show the desired release properties.

If the concentration of active ingredient (I) in the tablets from example 6-1 is increased around 3-fold, which produces the tablets from example 6-3, these tablets from example 6-3 do not fulfil the release properties after the preparation of the tablets.

Slight variations in the proportion of disintegration promoter, as shown in example 6-4, do not change the release characteristics of the tablet. A considerable influence on the release properties is seen after replacing the filler lactose monohydrate by mannitol (example 6-5) or by sole use of mannitol as filler (examples 6-6 and 6-7). Although these three formulations also contain magnesium stearate as lubricant and examples 6-6 and 6-7 also contain polyethylene glycol in the coating, the release from the tablets is good following preparation. Here, the negative influence of the magnesium stearate and the polyethylene glycol first becomes noticeable during the course of the stress test (example 6-6).

Based on examples 6-8, 6-9 and 6-10, the influence of magnesium stearate becomes significant on storage under humid conditions. All three tablet examples are free of lactose and polyethylene glycol; they vary exclusively in the type of lubricant. Only the magnesium stearate-containing formulation fails to meet the release requirements following one month in storage (example 6-8).

Examples 6-11 and 6-12 contain ca. 20% active ingredient (I) in the granulate, no lactose and no magnesium stearate in the tablet core and no polyethylene glycol in the film coating. The latter fulfil the release requirements both after preparation and after 1 month in open storage under humid conditions.

Examples 6-13 and 6-14 confirm the suitability of mixer granulation as the second wet granulation method for preparing granules/tablets with active ingredient (I). Directly after preparation, the tablets show the desired release profile.

Examples 6-16, 6-17 and 6-19 systematically investigate the influence of the active ingredient concentration in the granules (between 15% and 30%) using lactose monohydrate as auxiliary. Even the most dilute formulation (example 6-17) after preparation of the tablets does not show the desired release characteristics.

In contrast, formulations 6-15, 6-18 and 6-21, in which lactose monohydrate was replaced by mannitol, show the desired release profile.

Example 6-20 confirms the suitability of dry granulation as a further granulation method for preparing granules/tablets with active ingredient (I). Following preparation, the tablets show the desired release profile.

As the data show in the tables for release after preparation of the tablets (under 7.) and for release after the stress test of the tablets (under 8.), only the tablets with high concentrations of active ingredient (I) which contain no lactose, no magnesium stearate and no polyethylene glycol, surprisingly have the desired release profile. These are the tablets from examples 6-9, 6-10, 6-11, 6-12, 6-15, 6-18 and 6-21.

These surprising properties are most apparent when comparing the tablets from examples 6-6, 6-8 and 6-16, which do not show the desired release profile, with the tablets from examples 6-9 and 6-10.

The invention claimed is:

1. A solid pharmaceutical dosage form for oral administration comprising sodium 1-[6-(morpholin-4-yl)pyrimidin-4-yl]-4-(1H-1,2,3-triazol-1-yl)-1H-pyrazol-5-olate (active ingredient (I)), characterized in that
   (a) no binders, fillers and dry binders, disintegration promoters and lubricants having divalent and/or trivalent cations are present,
   (b) no lactose is present,
   (c) the concentration of active ingredient (I) is ≥10% based on the total mass of the formulation, and
   (d) if the dosage form has a film coating, the film coating does not comprise polyethylene glycol.

2. The solid pharmaceutical dosage form of claim 1, characterized in that at least 85% of active ingredient (I) is released per test specimen into the release medium after 30 minutes, from 6 test specimens relating to the pharmaceutical dosage form, according to the release method of the European Pharmacopoeia using apparatus 2 (paddle).

3. The solid pharmaceutical dosage form of claim 2, characterized in that the release medium consists of 900 ml of 0.1N hydrochloric acid.

4. The solid pharmaceutical dosage form of claim 1, characterized in that the dosage form is a tablet.

5. The solid pharmaceutical dosage form of claim 1, characterized in that the active ingredient (I) is 10 to 40% by weight based on the total mass of the formulation.

6. The solid pharmaceutical dosage form of claim 1, characterized in that at least one filler and at least one lubricant are present as auxiliaries.

7. The solid pharmaceutical dosage form of claim 6, characterized in that the filler is microcrystalline cellulose or mannitol or a mixture of microcrystalline cellulose and mannitol.

8. The solid pharmaceutical dosage form of claim 6, characterized in that the lubricant is sodium stearyl fumarate or glyceryl distearate.

9. The solid pharmaceutical dosage form of claim 4, characterized in that the tablet has a film coating.

10. A method of making a solid pharmaceutical dosage form for oral administration comprising sodium 1-[6-(morpholin-4-yl)pyrimidin-4-yl]-4-(1H-1,2,3-triazol-1-yl)-1H-pyrazol-5-olate (active ingredient (I)), characterized in that (a) no binders, fillers and dry binders, disintegration promoters and lubricants having divalent and/or trivalent cations are present, (b) no lactose is present, and (c) a concentration of active ingredient (I) is ≥10% based on the total mass of the formulation, further characterized in that
   (d) a granulate comprising the active ingredient (I) is initially prepared and
   (e) the granulate, optionally with addition of pharmaceutically acceptable auxiliaries, is then converted into the pharmaceutical dosage form.

11. The method of claim 10, characterized in that the granulate is prepared by wet granulation.

12. The method of claim 11, characterized in that fluidized bed granulation is used as the wet granulation method.

* * * * *